(12) United States Patent
Ogura (10) Patent No.: US 11,454,605 B2
(45) Date of Patent: Sep. 27, 2022

(54) IMAGE FORMING METHOD AND IMPEDANCE MICROSCOPE

(71) Applicant: National Institute of Advanced Industrial Science and Technology, Tokyo (JP)

(72) Inventor: Toshihiko Ogura, Tsukuba (JP)

(\*) Notice: Subject to any disclaimer, the term of this patent is extended or adjusted under 35 U.S.C. 154(b) by 25 days.

(21) Appl. No.: 17/253,115

(22) PCT Filed: Apr. 22, 2019

(86) PCT No.: PCT/JP2019/017069
§ 371 (c)(1),
(2) Date: Dec. 17, 2020

(87) PCT Pub. No.: WO2019/244468
PCT Pub. Date: Dec. 26, 2019

(65) Prior Publication Data
US 2021/0270758 A1 Sep. 2, 2021

(30) Foreign Application Priority Data

Jun. 20, 2018 (JP) .............................. JP2018-117279

(51) Int. Cl.
*G01N 27/02* (2006.01)
*H01J 37/22* (2006.01)
(Continued)

(52) U.S. Cl.
CPC ............ *G01N 27/02* (2013.01); *H01J 37/222* (2013.01); *H01J 37/244* (2013.01); *H01J 37/28* (2013.01);
(Continued)

(58) Field of Classification Search
CPC ............ G01N 27/02; G01N 33/48707; G01N 23/2251; H01J 37/222; H01J 37/244;
(Continued)

(56) References Cited

U.S. PATENT DOCUMENTS 2,879,394 A \* 3/1959 Pedersen ............... H01J 37/224
324/123 R
3,629,575 A \* 12/1971 Rakels ................... H01J 37/04
850/9
(Continued)

FOREIGN PATENT DOCUMENTS

JP 2008-076143 4/2008
JP 2011-089846 5/2011
(Continued)

OTHER PUBLICATIONS

Toshihiko Ogura, "Development of New Visualizing Technology of the Liquid Samples Based on Scanning Electron Microscopy", Oleoscience, 2015, p. 511-p. 516, vol. 15 No. 11.
(Continued)

*Primary Examiner* — David A Vanore
(74) *Attorney, Agent, or Firm* — Soei Patent & Law Firm (57) ABSTRACT

An image forming method includes: arranging a sample between a first main surface of an insulating thin film and a counter electrode, measuring an impedance value by inputting an AC potential signal to the counter electrode, scanning a physical beam while focusing and irradiating a conductive thin film given to cover a second main surface of the insulating thin film with the physical beam to lower an insulation property of the insulating thin film directly below an irradiation position, guiding the AC potential signal to the irradiation position, and forming an image from the impedance value corresponding to the irradiation position.

19 Claims, 12 Drawing Sheets

(51) Int. Cl.
*H01J 37/244* (2006.01)
*H01J 37/28* (2006.01)

(52) U.S. Cl.
CPC ............ *H01J 2237/24564* (2013.01); *H01J 2237/2803* (2013.01); *H01J 2237/2813* (2013.01)

(58) Field of Classification Search
CPC ............ H01J 37/28; H01J 2237/24564; H01J 2237/2803; H01J 2237/2813; H01J 2237/2008
See application file for complete search history.

(56) References Cited

U.S. PATENT DOCUMENTS

| | | | | |
|---|---|---|---|---|
| 5,898,176 | A * | 4/1999 | Mori | G01Q 30/02 850/10 |
| 7,888,143 | B1 * | 2/2011 | Keating | G01R 31/2837 438/18 |
| 2008/0224922 | A1 * | 9/2008 | Cleland | G01N 15/1056 342/175 |
| 2009/0196490 | A1 * | 8/2009 | Matsumiya | G06T 7/001 382/149 |
| 2012/0103817 | A1 | 5/2012 | Omori et al. | |
| 2012/0321037 | A1 | 12/2012 | Ogura | |
| 2015/0380210 | A1 * | 12/2015 | Budach | H01J 37/28 250/307 |
| 2016/0056012 | A1 | 2/2016 | Ogura | |
| 2018/0158648 | A1 * | 6/2018 | Tone | H01J 37/244 |
| 2019/0049399 | A1 | 2/2019 | Ogura | |
| 2021/0270758 | A1 * | 9/2021 | Ogura | G01N 33/48707 |

FOREIGN PATENT DOCUMENTS

| | | |
|---|---|---|
| JP | 2011-174784 | 9/2011 |
| JP | 2012-098063 | 5/2012 |
| JP | 2014-203733 | 10/2014 |
| WO | 2017/154936 | 9/2017 |

OTHER PUBLICATIONS

Toshihiko Ogura, "Direct observation of unstained wet biological samples by scanning-electron generation X-ray microscopy", Biochemical and Biophysical Research Communications, 2010, p. 198-p. 202, vol. 391.
Toshihiko Ogura, "Direct observation of unstained biological specimens in water by the frequency transmission electric-field method using SEM", PLoS One, 2014, p. 1-p. 6, vol. 9, issue 3, e92780.
International Search Report dated Jun. 4, 2019 for PCT/JP2019/017069.
International Preliminary Report on Patentability with Written Opinion dated Dec. 22, 2020 for PCT/JP2019/017069.
Toshihiko Ogura, "Development of New Visualizing Technology of the Liquid Samples Based on Scanning Electron Microscopy", Japan Oil Chemists' Society, 2015, p. 13-p. 18, vol. 15 No. 11.
Toshihiko Ogura et al., "Nanoscale Imaging of the Biological Samples in Water Using New Dielectric Microscope", Apr. 30, 2018, p. 42-p. 46, vol. 53.

* cited by examiner

PHASE IMAGE
(10000 MAGNIFICATION)

IMAGE FORMING METHOD AND IMPEDANCE MICROSCOPE

CROSS-REFERENCE TO RELATED APPLICATIONS

This application is a 35 U.S.C. § 371 national phase application of PCT/JP2019/017069, filed on Apr. 22, 2019, which claims priority to Japanese Patent Application No. 2018-117279, filed on Jun. 20, 2018.

TECHNICAL FIELD

The present invention relates to an image forming method and a microscope capable of observing an organic sample in a solution as it is with high resolution and more particularly to an image forming method and an impedance microscope capable of obtaining an image of an organic sample with high resolution by impedance measurement.

BACKGROUND ART

An optical microscope is widely used as a device for observing an organic sample in a solution. The resolution of the optical microscope is suppressed to about 200 nm due to the diffraction limit of the light. On the other hand, an electron microscope using an electron beam can acquire a high resolution of 10 nm or less. On the other hand, since an electron beam is used, it is necessary to evacuate the inside of the mirror body of the microscope, and in the observation of the organic sample in a solution, it is also necessary to enclose this in a capsule or the like capable of maintaining the atmospheric pressure. In addition, in order to reduce the damage to the organic sample due to electron beam irradiation and to obtain an image with high contrast, cumbersome pretreatment such as fixing of the sample with formaldehyde or the like, coating with gold or the like, and staining with a heavy metal may be required.

Patent Literature 1 and Non Patent Literature 1 disclose an observation method of an organic sample (biological sample) in a solution which is a kind of an X-ray microscope using a soft X-ray which is a characteristic X-ray generated by irradiating a metal thin film with an electron beam. In such a method, the sample is not directly irradiated with the electron beam, and without causing irradiation damage and without pretreatment such as staining for observing the biological sample, it is possible to observe the biological sample with high contrast.

In addition, Patent Literature 2 and Non Patent Literature 2 propose a variable potential transmission observation method that observes a biological sample by irradiating a heavy-metal thin film with an electron beam to locally generate a potential change and detecting a potential of the counter side. Generally, an organic sample (biological sample) has a relative permittivity of about 2 to 3, which is much lower than that of a solution (aqueous solution) which is about 80. For this reason, the permeation of the potential change is inhibited more in the organic sample (biological sample) than in the solution (aqueous solution). That is, it is possible to observe the biological sample by imaging the attenuation of the potential change while the biological sample passes through. Even in this case, it is possible to observe the biological sample in solution with high contrast without pretreatment such as staining.

CITATION LIST

Patent Literature

Patent Literature 1: Japanese Unexamined Patent Publication No. 2011-174784
Patent Literature 2: Japanese Unexamined Patent Publication No. 2014-203733

Non Patent Literature

Non Patent Literature 1: T. Ogura, "Direct observation of unstained wet biological samples by scanning-electron generation X-ray microscopy", Biochemical and Biophysical Research Communications, Vol. 391, pp. 198-202 (2010)
Non Patent Literature 2: T. Ogura, "Direct observation of unstained biological specimens in water by the frequency transmission electric-field method using SEM", PLOS ONE Vol. 9, e92780 (6pp) (2014)

SUMMARY OF INVENTION

Technical Problem

In the above-mentioned microscopic observation method using variable potential transmission, it is possible to observe a biological sample in a solution in a living state with high contrast and high resolution without damage of the electron beam. On the other hand, although it is not possible to analyze the composition of the sample, and in a case where the sample can be analyzed three-dimensionally, the above-mentioned microscopic observation method can be applied to an explanation of the structure and function of biological samples, development of organic materials, and the like.

The present invention has been made in view of the above circumstances, and an object thereof is to provide an image forming method and a microscope capable of observing a sample such as an organic material as it is with high resolution and capable of performing composition analysis.

Solution to Problem

The present inventor has conceived an impedance microscope that observes a sample by measuring impedance when an AC is applied so as to propagate an AC potential signal to an organic sample. In particular, when a conductive thin film covering an insulating thin film is focused and irradiated with an electron beam, an insulation property in a local, minute region of the insulating thin film is lowered. At this time, it was thought that extremely high resolution information could be obtained by measuring the impedance by applying the AC to facing conductive electrodes.

Specifically, according to the present invention, there is provided an image forming method including: an arrangement step of arranging a sample between a first main surface of an insulating thin film and a counter electrode; a measurement step of measuring an impedance value by inputting an AC potential signal to the counter electrode, scanning a physical beam while focusing and irradiating a conductive thin film given to cover a second main surface of the insulating thin film with the physical beam to lower an insulation property of the insulating thin film directly below an irradiation position, and guiding the AC potential signal to the irradiation position; and an image formation step of forming an image from the impedance value corresponding to the irradiation position.

According to the invention, it is possible to measure an impedance value of a sample as it is and form an image with high resolution.

In addition, according to the present invention, there is provided an impedance microscope in which a sample is arranged between a first main surface of an insulating thin film and a counter electrode, in which an impedance value is measured by inputting an AC potential signal to the counter electrode, scanning a physical beam while focusing and irradiating a conductive thin film given to cover a second main surface of the insulating thin film with the physical beam to lower an insulation property of the insulating thin film directly below an irradiation position, and guiding the AC potential signal to the irradiation position, and in which an image is formed from the impedance value corresponding to the irradiation position.

According to the invention, it is possible to measure the impedance value by setting the sample as it is, and it is possible to obtain the image with high resolution.

In the above-described invention, the sample may be given in a solution. According to the invention, it is possible to easily obtain the image with high resolution by easily giving a difference in the propagation of the AC potential signal with respect to the sample.

In the above-described invention, the counter electrode may include a second insulating thin film facing the first main surface of the insulating thin film, and an electric dipole may be formed at an interface with the solution in contact with the second insulating thin film. According to the invention, the AC potential signal is propagated across the insulating thin film by the electric dipole, and thus, the observation with high resolution is enabled.

In the above-described invention, the counter electrode may include a conductive thin film electrode given along a back surface of the second insulating thin film, and the AC potential signal may be input to the conductive thin film electrode. According to the invention, it is possible to input the AC potential signal along the surface of the conductive thin film electrode in response to the scanning of the physical beam.

In the above-described invention, the counter electrode may include a probe directed into the solution, and the AC potential signal may be input to the probe. According to the invention, the position on the counter electrode side can be limited, and thus, the observation with high resolution is enabled.

In the above-described invention, the physical beam may be an electron beam or a laser beam. According to the invention, since an apparatus of the related art can be utilized as an irradiation source, the cost can be reduced, and the observation with high resolution is enabled.

In the above-described invention, a sinusoidal wave or noise including a plurality of frequency components may be applied as the AC potential signal, and a frequency spectrum may be obtained from the detected AC signal. Further, the frequency component of the detected AC signal may be synchronously detected and separated to obtain the frequency spectrum. According to the invention, a composition of the sample can be analyzed based on the frequency spectrum, and further, a minute AC potential signal can be detected, so that more accurate analysis of the composition is enabled.

In the above-described invention, a bias voltage may be applied to the conductive thin film, a DC component may be cut off, and after that, only an AC signal component may be extracted to obtain phase information together with impedance information. According to the invention, it is possible to obtain the AC potential signal with high sensitivity.

In the above-described invention, a bias voltage may be applied to the conductive thin film, the bias voltage may also be applied to the conductive thin film electrode, an AC signal component of the conductive thin film may be extracted, and phase information may be obtained together with impedance information. Further, pre-controlling of extracting the AC signal component while changing the bias voltage and setting the bias voltage so that the SN ratio is a predetermined value is given. According to the invention, a wider range of observation is enabled by obtaining the phase information of the AC potential signal, and more accurate analysis with a good SN ratio is enabled.

The above-described invention may further include an image control unit that controls the frequency of the AC potential signal input to the conductive thin film electrode to a value equal to or greater than that obtained by dividing the total number of pixels of the image by the number of seconds of the imaging time. According to the invention, it is possible to reliably obtain the impedance values for all pixels.

In the above-described invention, in the counter electrode, metal pattern electrodes may be arranged in an array shape along a back surface of the second insulating thin film, AC potential signals having different frequency components may be input to the respective metal pattern electrodes, and three-dimensional structure information may be obtained from an inclined image based on a mutual angle between a position of the metal pattern electrode and the irradiation position. According to the invention, it is possible to observe the organic sample three-dimensionally.

DESCRIPTION OF EMBODIMENTS

First Embodiment

Hereinafter, one embodiment of an image forming method and an impedance microscope of observing an organic sample according to the present invention will be described with reference to FIGS. 1 and 2.

Figure 1:
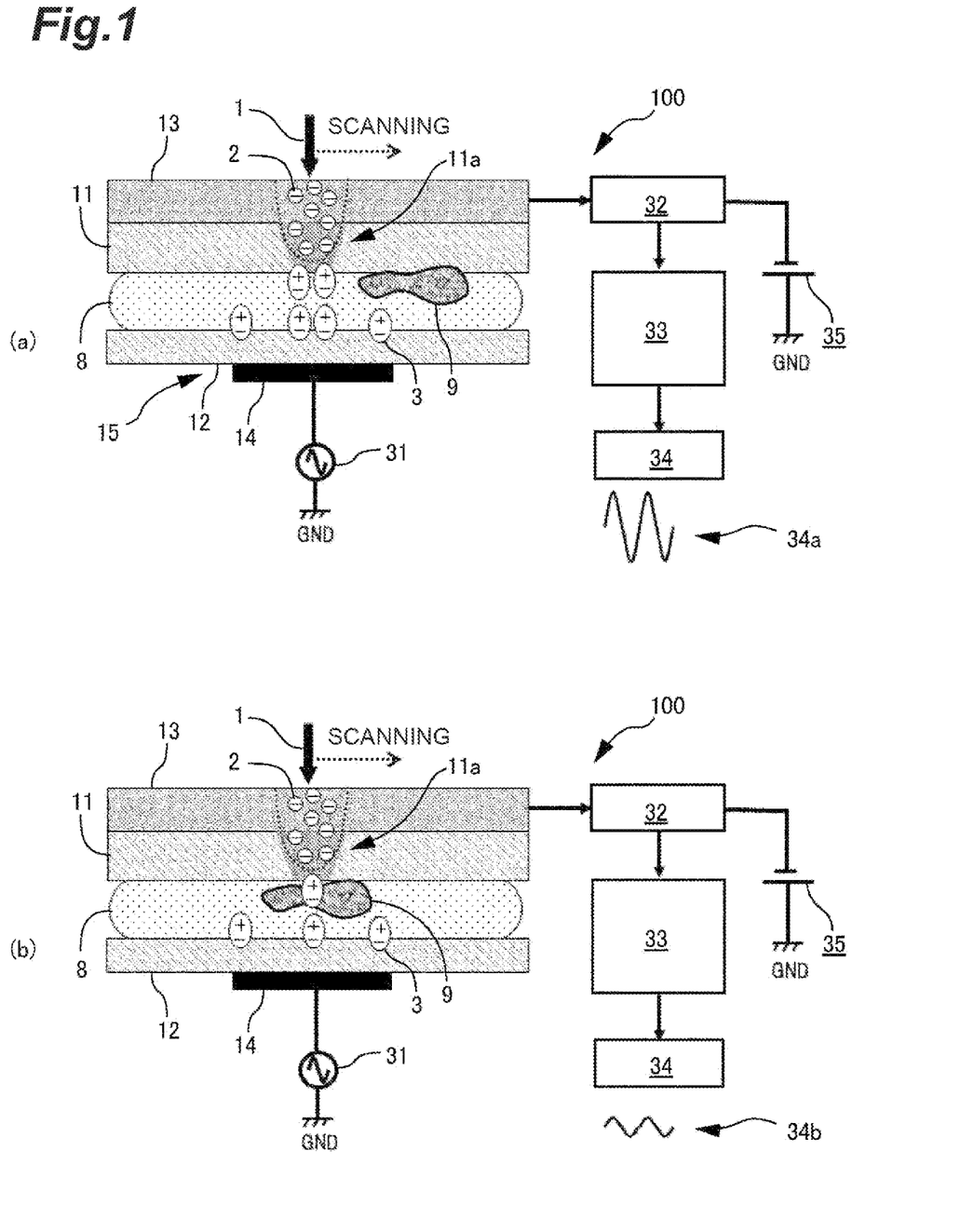
FIG. 1 is a block diagram of an impedance microscope according to an embodiment of the present invention.

As illustrated in FIG. 1, an impedance microscope 100 includes a first insulating thin film 11 of the upper side and a counter electrode 15 facing a main surface orienting downward, from the lower side. The upper side surface of the first insulating thin film 11 is covered with a conductive thin film 13. In addition, the counter electrode 15 includes a second insulating thin film 12 of which upper side surface is located so as to face the lower side surface of the first insulating thin film 11. The counter electrode 15 further includes a conductive thin film electrode 14 given along a back surface of the second insulating thin film 12. An organic sample 9 is arranged between the first insulating thin film 11 and the counter electrode 15 and is held by the solution 8. Typically, the solution 8 is interposed between the first insulating thin film 11 and the second insulating thin film 12 to fill the organic sample.

The conductive thin film 13 is provided with a physical beam irradiator (not illustrated) such as an electron gun capable of focusing and irradiating with the physical beam 1 from above and scanning the physical beam 1 along the surface of the conductive thin film 13. As the physical beam 1, an electron beam or a laser beam can be used, and the physical beam 1 can destroy the insulation of the first insulating thin film 11 directly below the irradiation position and form an insulation property lowered region 11a of which insulation property is lowered by irradiating the conductive thin film 13. For example, in a case where irradiation with the electron beam is performed, the incident electrons 2 are scattered and absorbed by the first insulating thin film 11 directly below the irradiation position to form the insulation property lowered region 11a. As the physical beam 1, other charged particle beams such as an ion beam, a neutron beam, and a positron beam can also be used.

On the other hand, a signal output device 31 such as a function generator is connected to the conductive thin film electrode 14 of the counter electrode 15, and the AC potential signal is input. The AC potential signal allows an electric dipole 3 to be formed at the interface between the second insulating thin film 12 and the solution 8 and is propagated by the formation of the electric dipole 3. In addition, an AC amplifier 32 that amplifies the detected AC signal is connected to the conductive thin film 13, and an output signal 34 can be obtained through a bandpass filter 33. That is, the AC potential signal is guided to the insulation property lowered region 11a of the first insulating thin film of which insulation property is lowered at the position directly below the irradiation region of the physical beam 1, the AC signal attenuated in the process of being guided through the conductive thin film 13 is detected and amplified by the AC amplifier 32, and the output signal 34 having a frequency in a necessary range can be extracted by cutting an unnecessary frequency band by the bandpass filter 33.

Accordingly, the impedance value is measured from the extracted output signal 34, and the image is formed from the impedance value corresponding to each irradiation position by scanning the physical beam 1 described above. In addition, by applying a bias voltage 35 to the conductive thin film 13 through the AC amplifier 32, the sensitivity of the AC signal to be detected can be increased.

Incidentally, as illustrated in FIG. 1(a), when only the solution 8 (and the second insulating thin film 12) exists between the insulation property lowered region 11a and the conductive thin film electrode 14, in a case where, for example, water is set as the solution, the potential signal can be propagated well by increasing the relative permittivity to about 80, and thus, the attenuation of the AC potential signal guided to the insulation property lowered region 11a is reduced. For this reason, the amplitude of an output signal 34a is increased and the impedance value is decreased by reflecting the conductance component of water.

On the other hand, as illustrated in FIG. 1(b), for example, in a case where a biological sample configured with amino acids, lipids, or the like is set as the organic sample 9, the propagation of the potential signal is inhibited by lowering the relative permittivity to about 2 to 5, and thus, the attenuation of the AC potential signal guided to the insulation property lowered region 11a is increased. For this reason, the amplitude of an output signal 34b is decreased, and the impedance value is increased.

In this manner, the impedance value measured from the output signal 34 is small in a case where only the solution 8 is used, and the impedance value is large in a case where the potential signal is allowed to be propagated in the organic sample 9. Therefore, by forming the image corresponding to the irradiation position by the scanning of the physical beam 1 from the impedance value, it is possible to observe the organic sample 9 as an image. In addition, the size of the insulation property lowered region 11a depends on the irradiation diameter of the physical beam 1 which is to be irradiated. Therefore, it is possible to obtain an image with significantly higher resolution by narrowing down the physical beam 1 to a small size. In addition, since the irradiating with the physical beam 1 for lowering the insulation property of the insulating thin film and the inputting of the AC potential signal for measuring the impedance value are independent of each other and even the propagation in the insulation property lowered region 11a is sufficient, the AC potential signal can be allowed to be weak. Therefore, the organic sample 9 does not require any pretreatment and is insignificantly affected by the AC potential signal. In this manner, it is possible to observe the organic sample 9 in the solution 8 as it is by a significantly high-resolution image formed from the impedance value. In addition, the combination of the solution 8 and the organic sample 9 is not limited to water and the biological sample, and thus, it is possible to obtain an image of the organic sample 9 when the dielectric constants are different from each other.

Figure 2:
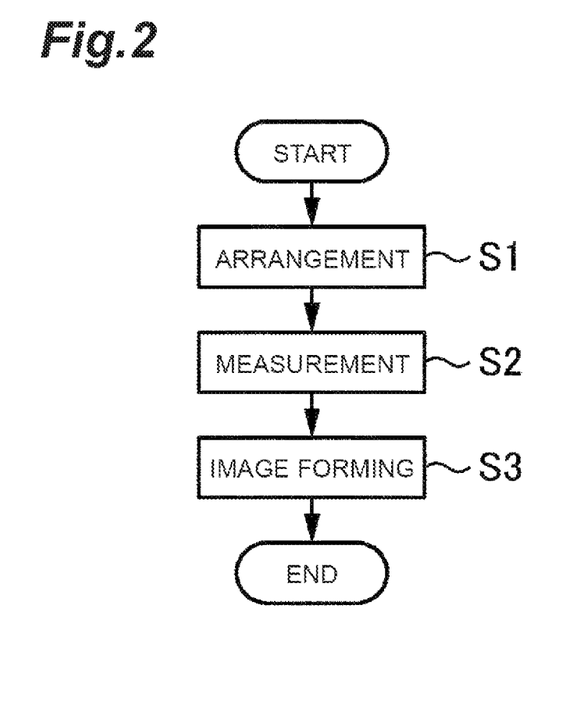
FIG. 2 is a flowchart of an image forming method according to an embodiment of the present invention.

That is, referring to FIG. 2 together, in the image forming method according to the present embodiment, first, in an arrangement step (S1), the organic sample 9 held in the solution 8 is arranged between the first insulating thin film 11 and the counter electrode 15. Next, in a measurement step (S2), the AC potential signal is input to the conductive thin film electrode 14 of the counter electrode 15, scanning of the physical beam 1 is performed while focusing and irradiating the conductive thin film 13 with the physical beam 1 from above the conductive thin film 13, and the impedance value is measured as described above. Specifically, the insulation property of the first insulating thin film 11 is lowered to form the insulation property lowered region 11a directly below the irradiation position irradiated with the physical beam 1. The AC potential signal input to the conductive thin film electrode 14 of the counter electrode 15 is guided to the insulation property lowered region 11a. The guided AC potential signal propagates through the solution 8 and the organic sample 9, and becomes an output signal 34 via the conductive thin film 13. Then, the impedance value is obtained from the output signal 34 corresponding to each irradiation position. Finally, in the image formation step (S3), an image is formed as described above based on the impedance value with respect to the irradiation position.

In addition, since the impedance includes resistance, inductance, and conductance, these components may be individually measured and imaged. In addition, the phase of the output signal may be obtained, and the phase may be imaged. Since the measurement result depends on the compositions and distances of the solution 8 and the organic sample 9 through which the AC potential signal propagates, the obtained image includes not only the shape but also the information on the composition of the organic sample 9.

In addition, although the AC amplifier 32 is connected to the conductive thin film 13 in the above-described embodiment, for example, the AC amplifier 32 is connected to the conductive thin film electrode 14, so that the image can also be obtained from the impedance value similarly.

Herein, it is preferable that the frequency of the AC potential signal input to the conductive thin film electrode 14 is set to a value equal to or greater than that obtained by dividing the total number of pixels of the image to be obtained by the number of seconds of the imaging time. That is, an AC potential signal having one or more wavelengths is input to all the pixels, and the output is obtained. For example, in a case where an image of 100×100 pixels is to be obtained by scanning for 10 seconds, since the irradiation time of the physical beam 1 per pixel is set to 1 msec, the frequency of 1 kHz or more, which is the reciprocal of the AC potential signal, is required. Accordingly, it is possible to reliably obtain the impedance value for all the pixels. For example, it is preferable to use a frequency of 1 MHz as the bandpass filter 33 by adding a sinusoidal wave having a frequency of 1 MHz as the AC potential signal, but it is possible to use a frequency of several kHz to several GHz.

In addition, as described above, the impedance microscope is suitable for the observation of an organic sample, not only an organic material but also a material having a dielectric constant different from that of a solution can be observed. For example, the sample may be made of a material such as a ceramic or a metal. In addition, the periphery of the sample is not necessarily filled with the solution, but may be filled with a substance having a dielectric constant different from that of the sample or a vacuum. For example, air or other atmospheres can be used relatively easily.

Second Embodiment

Next, another embodiment of the impedance microscope will be described with reference to FIGS. 3 and 4.

Figure 3:
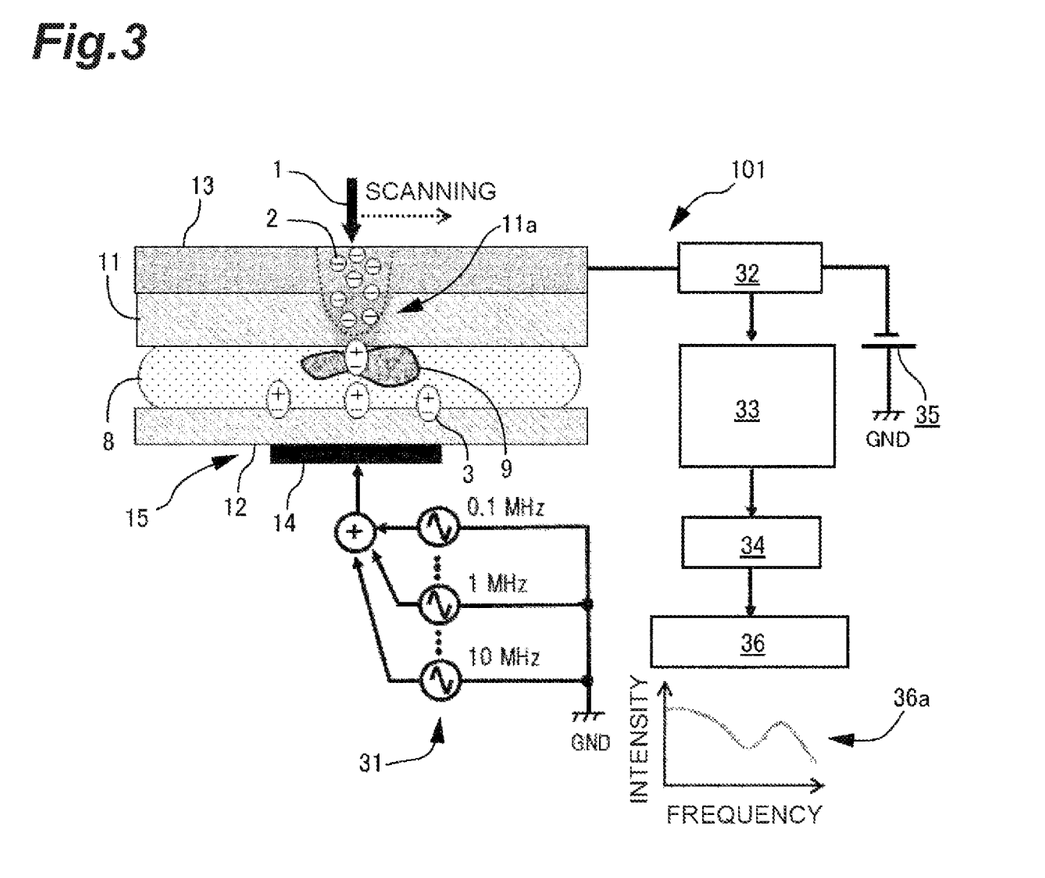
FIG. 3 is a block diagram of an impedance microscope according to a second embodiment.

As illustrated in FIG. 3, in an impedance microscope 101, the AC potential signal input to the conductive thin film electrode 14 is set to an AC potential signal in which a plurality of frequency components are superimposed. For example, sinusoidal waves having a plurality of predetermined frequencies are superimposed by the signal output device 31, the AC signal amplified by the AC amplifier 32 is divided into each frequency component by the bandpass filter 33 to obtain the impedance value for each frequency, and a frequency spectrum component 36a is detected by a spectrum measurement device 36. Since a difference in the composition of the organic sample 9 can be a difference in the frequency spectrum component 36a of the impedance value, it is also possible to estimate the composition of the organic sample 9. In addition, the other components are the same as in the first embodiment.

Figure 4:
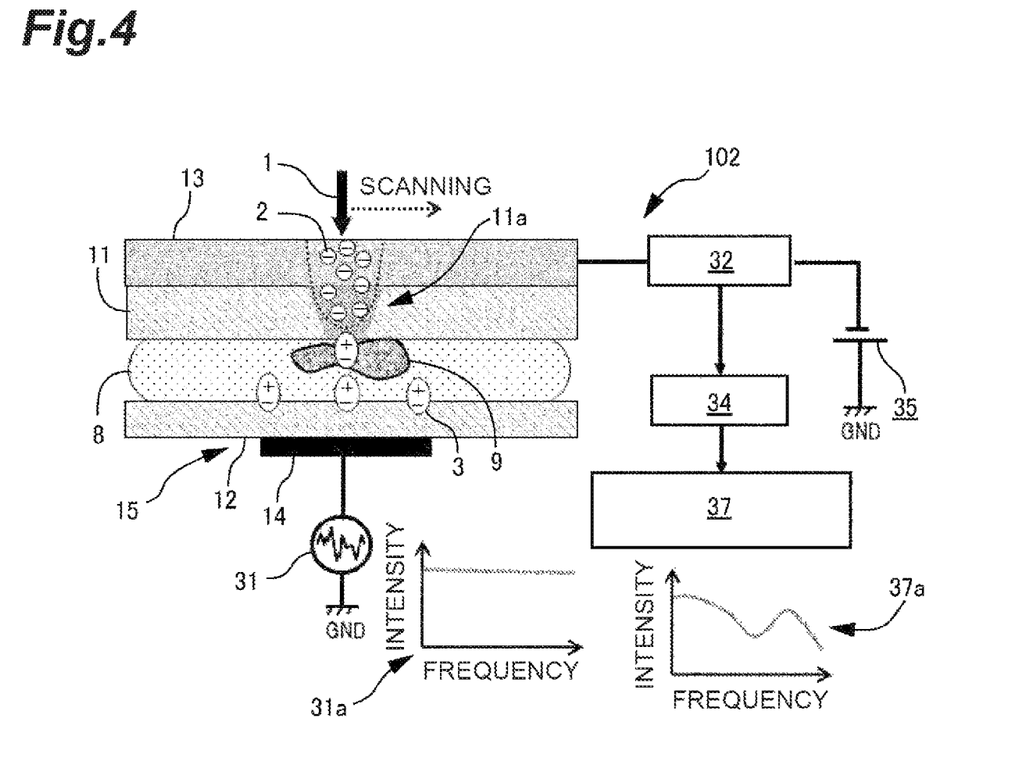
FIG. 4 is a block diagram of an impedance microscope in a modified example of the second embodiment.

In addition, as illustrated in FIG. 4, an impedance microscope 102 uses the AC potential signal which is to be input to the conductive thin film electrode 14 as noise including a plurality of frequency components. For example, white noise 31a can be input as the AC potential signal. In this case, the output signal 34 obtained from the AC signal amplified by the AC amplifier 32 is analyzed by a Fourier spectrum analyzer 37 to obtain a frequency spectrum 37a of the impedance value. Similarly, it is possible to estimate the composition of the organic sample 9 for this. In addition, the frequency components of the AC signal may be synchronously detected and separated to obtain the frequency spectrum.

Third Embodiment

Still another embodiment of the impedance microscope will be described with reference to FIGS. 5 and 6.

Figure 5:
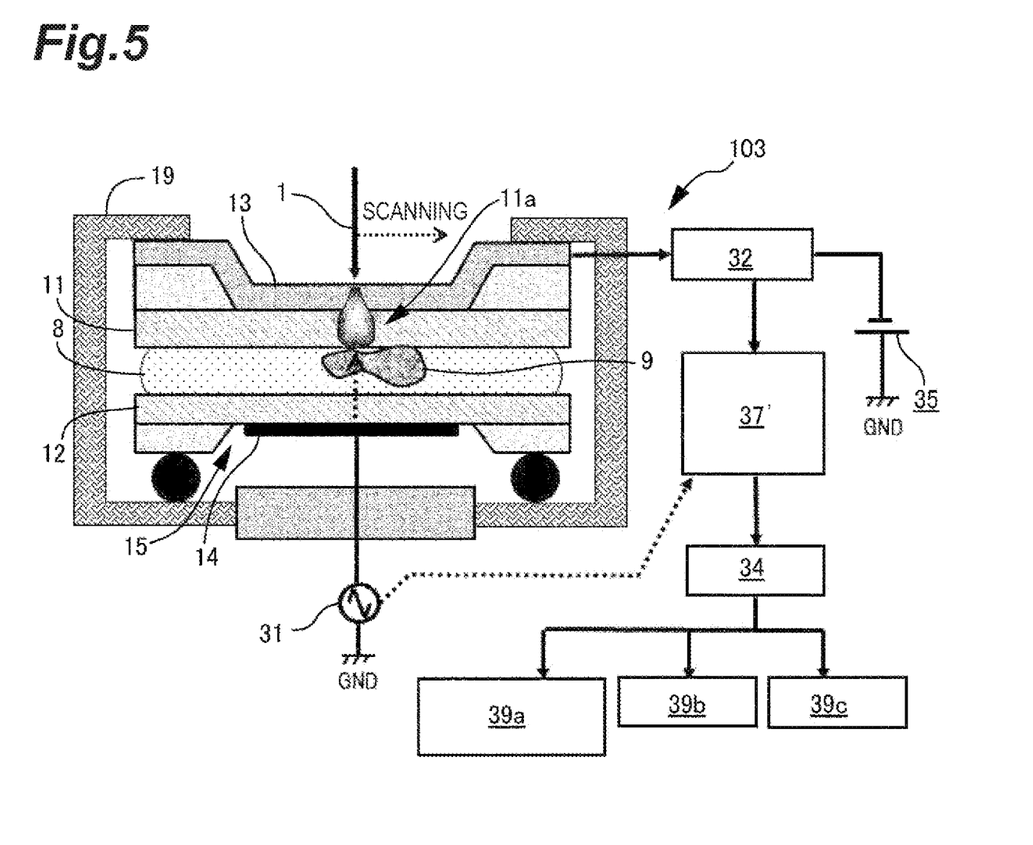
FIG. 5 is a block diagram of an impedance microscope according to a third embodiment.

As illustrated in FIG. 5, an impedance microscope 103 inputs the AC signal amplified by the AC amplifier 32 to a lock-in amplifier 37' to obtain the output signal 34, and impedance information, amplitude information, and phase information of the output signal can be obtained by an impedance measurement device 39a, an amplitude measurement device 39b, and a phase measurement device 39c, respectively. In the lock-in amplifier 37', noise can be significantly reduced by cutting off the DC component due to the applied bias voltage 35 and, after that, extracting only the AC signal component, and thus, by obtaining an output signal having an extremely high SN ratio, a high-definition image can be obtained very clearly. In addition, since the structure for holding the organic sample 9 including a holder 19 is known and the basic structure is the same as those of the other embodiments described above, detailed description thereof will be omitted.

Figure 6:
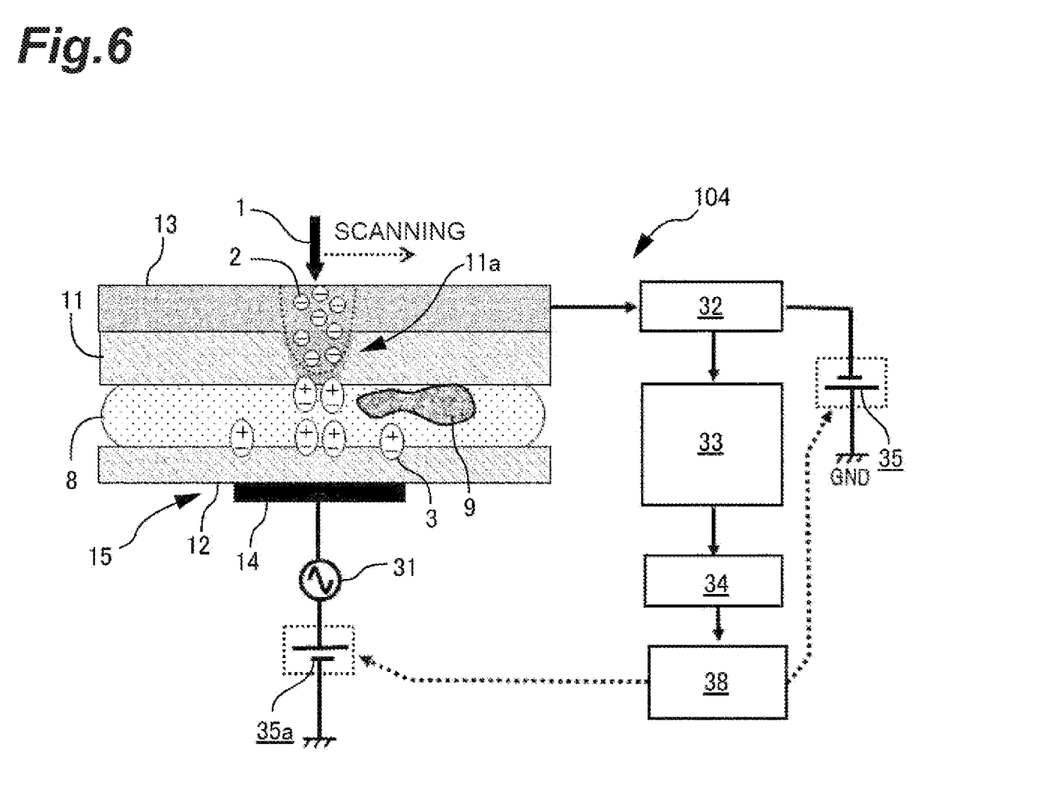
FIG. 6 is a block diagram of an impedance microscope in a modified example of the third embodiment.

As illustrated in FIG. 6, an impedance microscope 104 applies the bias voltage 35 to the conductive thin film 13 and also applies a second bias voltage 35a to the conductive thin film electrode 14. The bias voltage 35 and the second bias voltage 35a are both adjustable by a bias adjustment circuit 38. Then, the output signal is obtained by extracting only the AC signal component from the AC signal detected from the conductive thin film 13, and the impedance information and the phase information are obtained together from the output signal. Since the phase information also depends on the composition of the organic sample 9 through which the AC potential signals propagate, the composition information of the organic sample 9 is included. In addition, it is preferable to, before these, perform pre-controlling of measuring the output signal while changing the bias voltage 35 and the second bias voltage 35a, setting the SN ratio of the output signal equal to or greater than a predetermined value, and optimizing the output signal. At this time, the bias adjustment circuit 38 may be controlled so as to automatically perform such adjustment.

Fourth Embodiment

Further still another embodiment of the impedance microscope will be described with reference to FIGS. 7 and 8.

Figure 7:
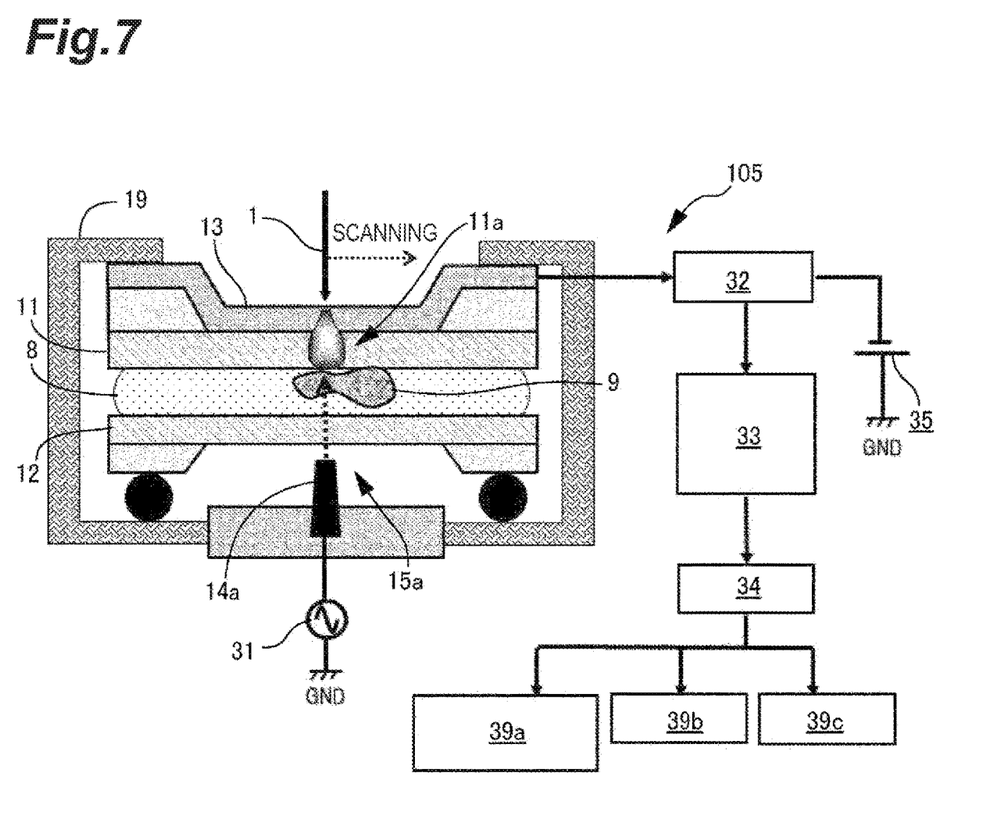
FIG. 7 is a block diagram of an impedance microscope according to a fourth embodiment.

As illustrated in FIG. 7, an impedance microscope 105 includes a needle-shaped probe 14a as a counter electrode 15a, and the AC potential signal is input to the probe. The probe 14a has a gap with respect to the second insulating thin film 12 and is directed into the solution 8. Even in a case where there is a gap in this manner, the AC potential signal propagates through the gap, and an image based on the impedance value or the like can be obtained. In addition, since the path of the AC potential signal includes the path from the tip of the probe 14a to the insulation property lowered region 11a corresponding to the irradiation position of the physical beam 1 of which position is changed based on the scanning, the inclined image based on the inclined path is obtained.

Figure 8:
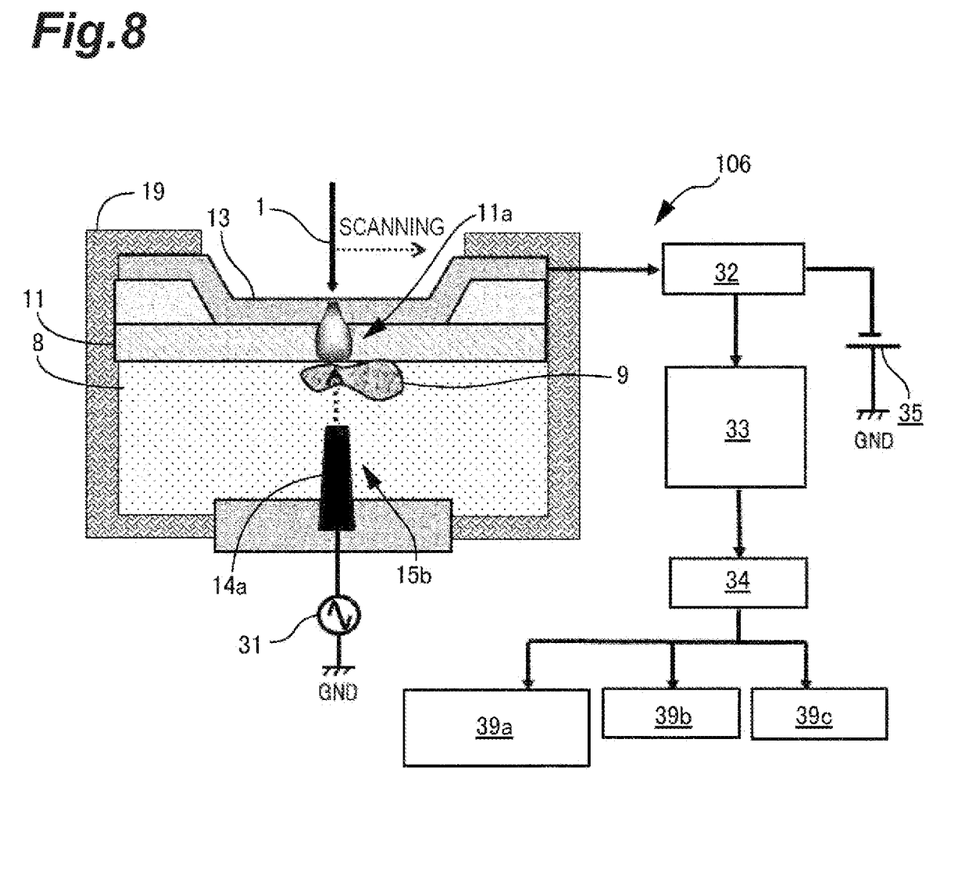
FIG. 8 is a block diagram of an impedance microscope in a modified example of the fourth embodiment.

In addition, as illustrated in FIG. 8, an impedance microscope 106 includes the needle-shaped probe 14a as a counter electrode 15b, and the tip thereof is arranged so as to project into the solution 8. That is, the second insulating thin film is removed in the holder 19, and thus, the lower portion of the first insulating thin film 11 is filled with the solution 8. Even In this case, it is possible to obtain the image based on the impedance value similarly to the case of the impedance microscope 105.

Fifth Embodiment

Yet another embodiment of the impedance microscope will be described with reference to FIG. 9.

Figure 9:
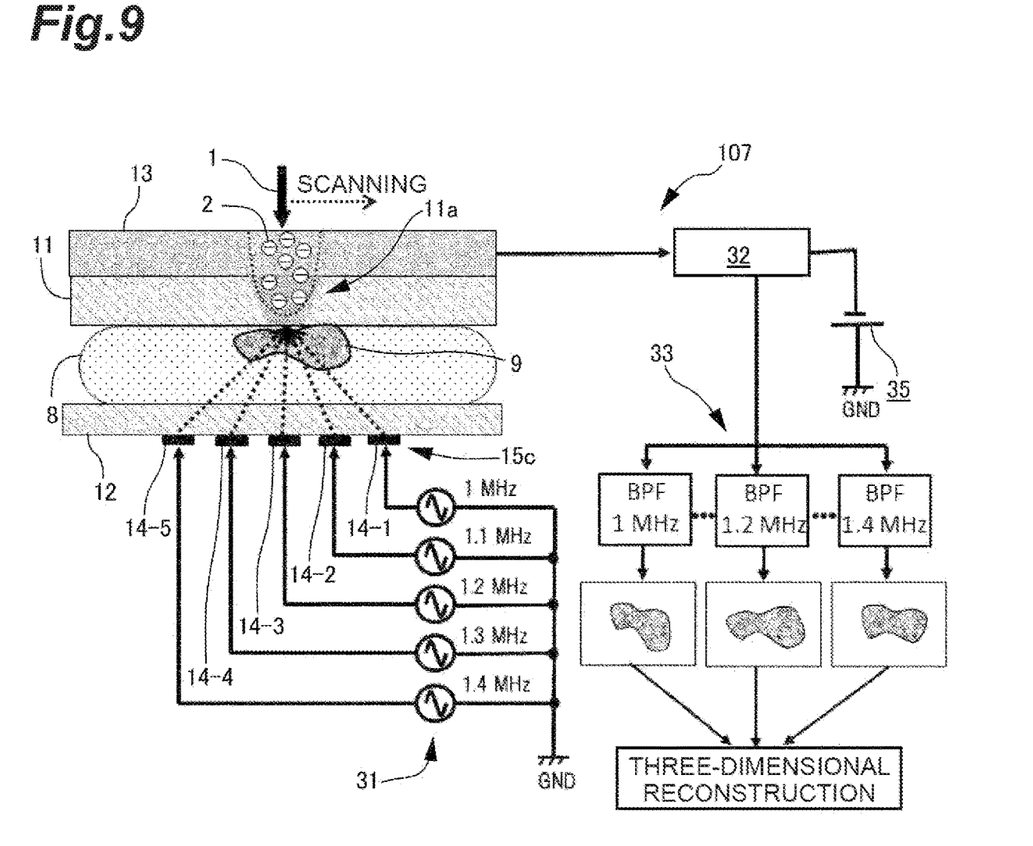
FIG. 9 is a block diagram of an impedance microscope according to a fifth embodiment.

As illustrated in FIG. 9, in an impedance microscope 107, a plurality of metal pattern electrodes 14-1 to 14-5 are arranged in an array shape along the back surface (lower side surface) of the second insulating thin film 12 as a counter electrode 15c. In terms of the illustration, the number of metal pattern electrodes is set to five, but in reality, the number of metal pattern electrodes may be increased, or the metal pattern electrodes may be arranged to be spread out in a two-dimensional shape. The AC potential signals having different frequency components are input from the signal output device 31 to each of the metal pattern electrodes 14-1 to 14-5. The AC signal amplified by the AC amplifier 32 is frequency-separated by the bandpass filter 33, and an image based on the impedance value and the phase can be formed for each frequency component. Each of these images becomes an inclined image based on the mutual angle between the position of a specific metal pattern electrode (for example, 14-1) and the irradiation position by the scanning of the physical beam 1. In addition, such an inclined image can be obtained from each of the metal pattern electrodes 14-1 to 14-5. That is, a plurality of the inclined images can be obtained in one scanning. Further, by combining a plurality of the inclined images, it is possible to obtain three-dimensional position information of the impedance value, and the inclined image can be reconstructed three-dimensionally. Accordingly, by obtaining three-dimensional structure information of the organic sample 9 in one scanning (imaging), that is, in a very short time, three-dimensional structure analysis is enabled.

Image Formation Result

The result of forming an image by using the impedance microscope 103 illustrated in the third embodiment will be described with reference to FIGS. 10 to 12.

Figure 10:
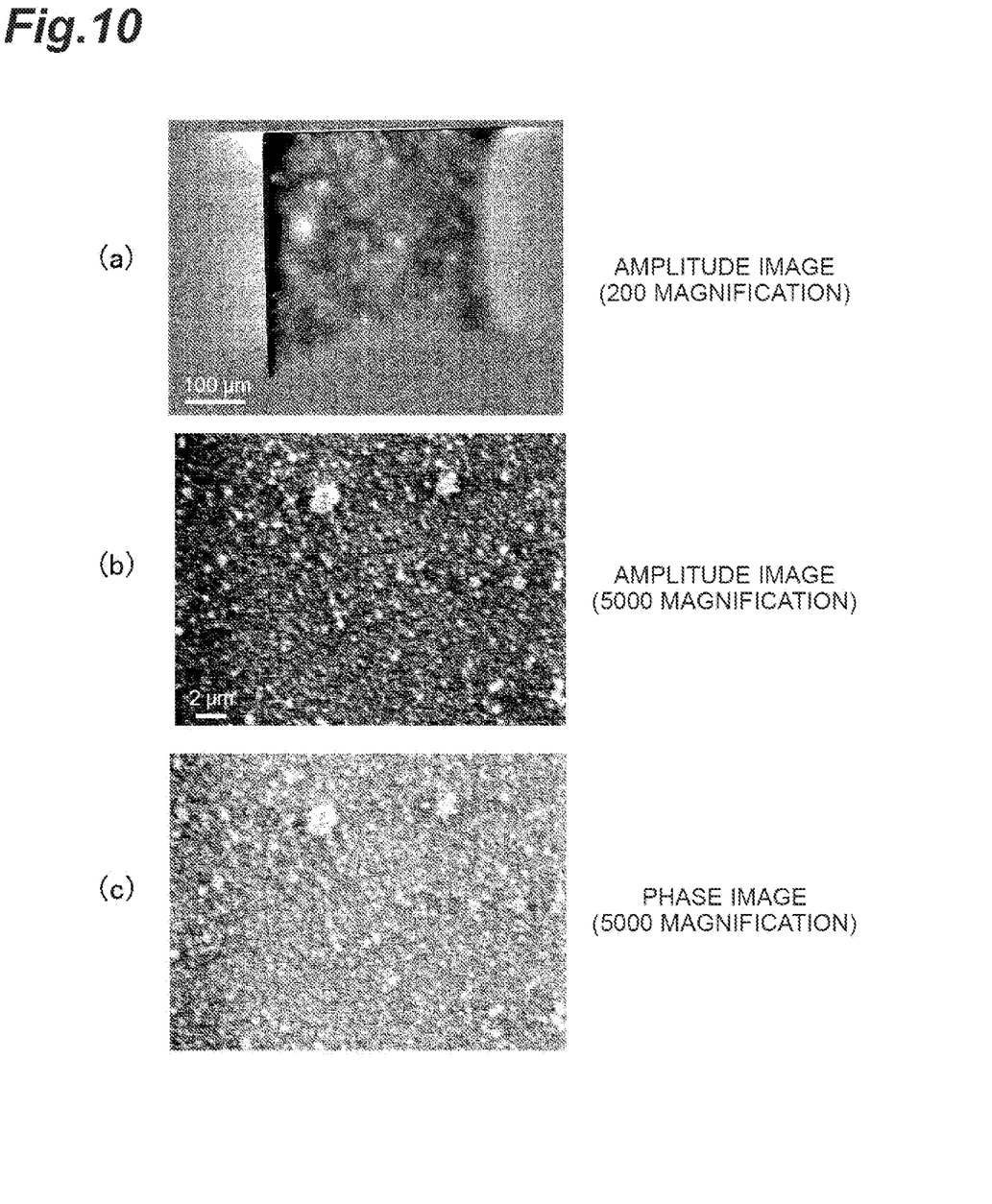
FIG. 10 is (a) a 200-magnification amplitude image, (b) a 500-magnification amplitude image, and (c) a 5000-magnification phase images of a bead sample having a diameter of 500 nm by an impedance microscope.

As shown in FIG. 10, water was set as the solution 8, a bead sample having a diameter of 500 nm was set as the organic sample 9, and images were formed for each of the amplitude and phase obtained from the amplitude measurement device 39b and the phase measurement device 39c (refer to FIG. 5). For example, it was possible to clearly form a high-definition image of 5000 magnification from the amplitude (refer to FIG. 10(b)). In addition, it was also possible to obtain an image from the phase similar to that from the amplitude (refer to FIG. 10(c)).

Figure 11:
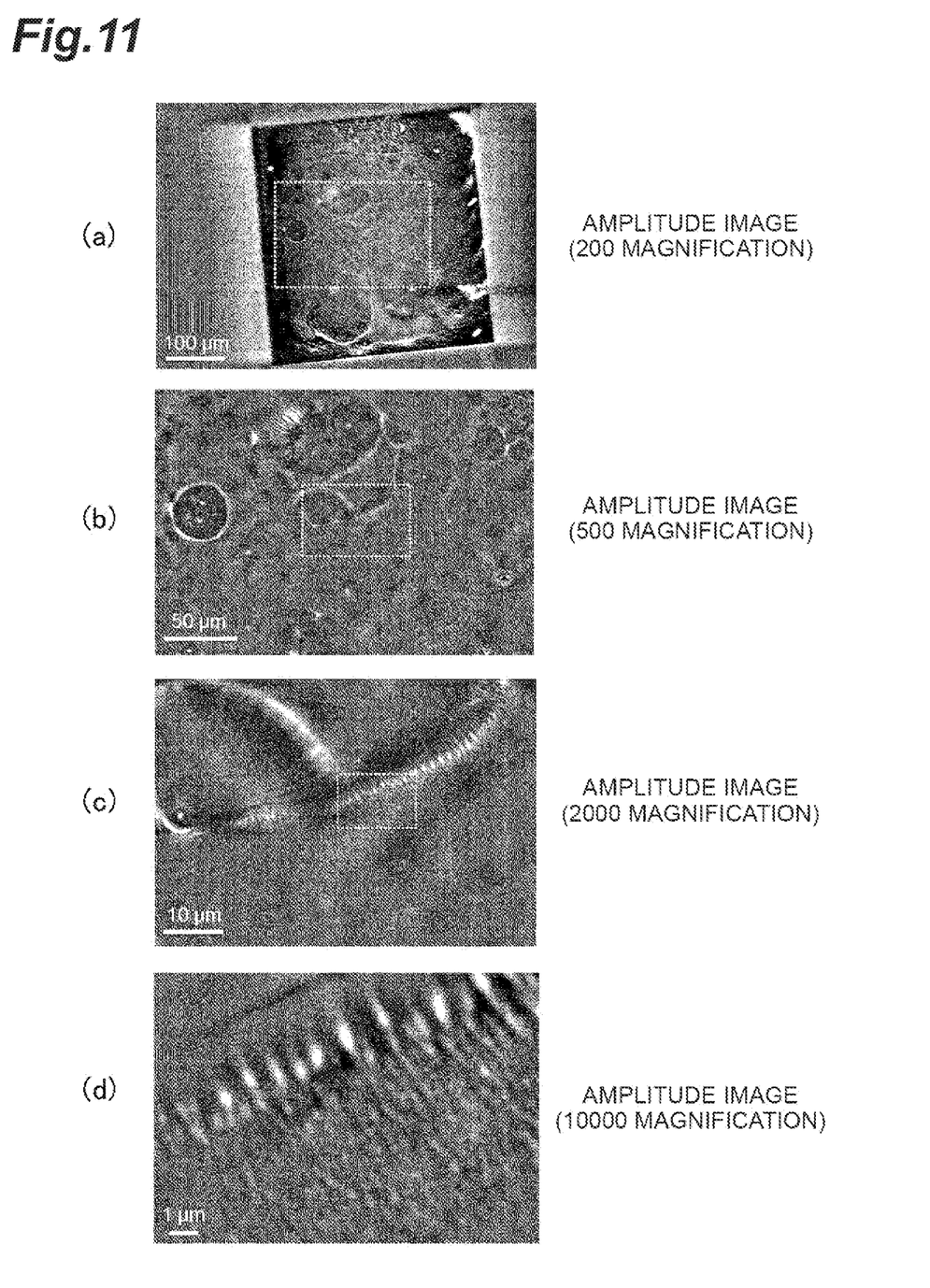
FIG. 11 is (a) 200-magnification, (b) 500-magnification, (c) 2000-magnification, and (d) 10000-magnification amplitude images of a bead sample having a diameter of 500 nm by an impedance microscope.

As shown in FIG. 11, water was set as the solution 8, and air was mixed to form an image near the interface between the water and the air. In the same manner as described above, a bead sample having a diameter of 500 nm was used as the organic sample 9, and an image for the amplitude obtained from the amplitude measurement device 39b was formed. The dotted lines in FIGS. 11(a), 11(b), and 11(c) indicate the fields of view of FIGS. 11(b), 11(c), and 11(d), respectively. Herein, it was possible to confirm that a high-definition image of 10000 magnification was clearly formed.

Figure 12:
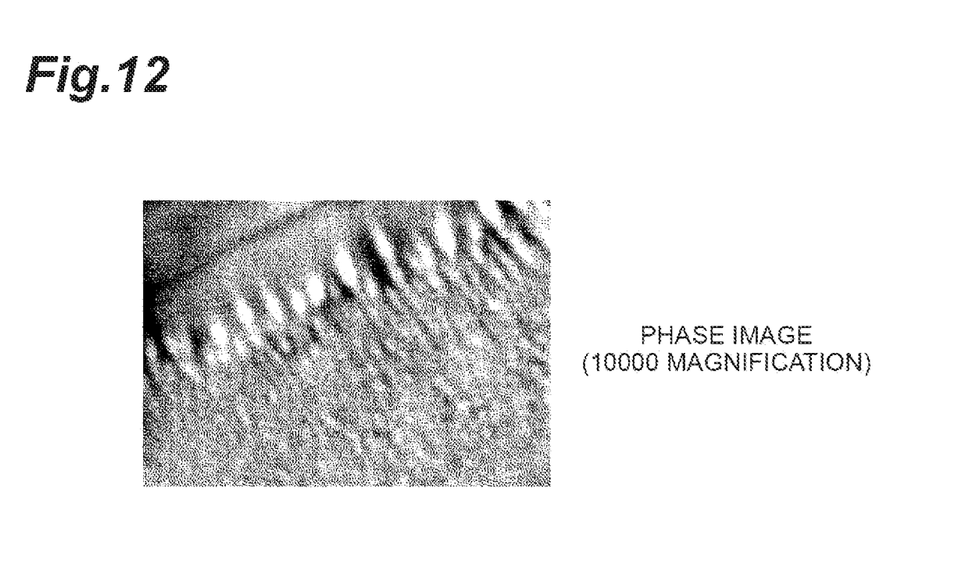
FIG. 12 is a 10000-magnification phase image of a bead sample having a diameter of 500 nm by an impedance microscope.

As shown in FIG. 12, in the image about the phase obtained from the phase measurement device 39c, it was possible to clearly form a high-definition image of 10000 magnification similarly.

While the examples according to the present invention and the modifications based on the present invention have been described above, the present invention is not necessarily limited to these, and those skilled in the art can find various alternative and modified examples without deviating from the spirit of the present invention or the scope of the attached claims.

REFERENCE SIGNS LIST

1: physical beam, 8: solution, 9: organic sample, 11: first insulating thin film, 12: second insulating thin film, 13: conductive thin film, 14: conductive thin film electrode, 15: counter electrode, 31: signal output device, 32: AC amplifier, 100: impedance microscope.

The invention claimed is:
1. A method of forming an image of a sample, the method comprising:
applying an AC potential signal to a counter electrode, wherein the sample is located between a first main surface of an insulating thin film and the counter electrode;
irradiating and scanning a conductive thin film disposed on a second main surface of the insulating thin film with a physical beam to form a localized region of the insulating thin film in which an insulation property is lowered;
acquiring an output signal associated with the AC potential signal guided to the conductive thin film via the localized region;
measuring an impedance value corresponding to the localized region based on the output signal; and
forming the image of the sample based on the impedance value.

2. The method according to claim 1, wherein
the counter electrode includes a conductive thin film electrode provided along a second insulating thin film, the first main surface of the insulating thin film facing the second insulating thin film, and
the AC potential signal is applied to the conductive thin film electrode.

3. The method according to claim 1, wherein the counter electrode includes a probe having a needle-shape, and the AC potential signal is applied to the probe.

4. The method according to claim 1, wherein
the AC potential signal applied to the counter electrode includes a plurality of frequency components, and
the method further comprises generating a frequency spectrum of the impedance value based on the output signal including the plurality of frequency components.

5. The method according to claim 4, wherein white noise is applied to the counter electrode as the AC potential signal.

6. The method according to claim 1, further comprising applying a bias voltage to the conductive thin film.

7. The method according to claim 6, further comprising removing a DC component from the AC potential signal guided to the conductive thin film by irradiation to obtain the output signal.

8. The method according to claim 6, further comprising:
applying a second bias voltage to the counter electrode; and
adjusting the bias voltage to the conductive film and the second bias voltage to the counter electrode so that an SN ratio of the output signal is equal to or greater than a predetermined value.

9. The method according to claim 1, wherein
the counter electrode includes a plurality of metal pattern electrodes arranged in an array on a second insulating thin film,
a plurality of images of the sample taken at different angles corresponding to a position of each of the plurality of metal pattern electrodes along the second insulating thin film are generated based on a plurality of impedance values measured from the output signal, and
three-dimensional structure information is generated based on the plurality of images.

10. The method according to claim 9, wherein
a plurality of AC potential signals having different frequency components are applied to the plurality of metal pattern electrodes, and
the method comprises separating the output signal into the different frequency components to measure the plurality of impedance values.

11. The method according to claim 1, wherein the impedance value includes resistance, inductance and conductance, and images of the sample are individually formed based on the resistance, the inductance, and the conductance.

12. The method according to claim 1, further comprising:
measuring phase information of the output signal; and
forming an image of the sample based on the phase information.

13. The method according to claim 1, wherein the AC potential signal has a frequency equal to or higher than a value obtained by dividing a total number of pixels of the image by a number of seconds to scan the image.

14. An impedance microscope comprising:
an insulating thin film having a first main surface and a second main surface;
a counter electrode facing the first main surface of the insulating thin film;
a conductive thin film disposed on the second main surface of the insulating thin film;
a physical beam irradiator to irradiate and scan the conductive thin film with a physical beam to form a localized region of the insulating thin film in which an insulation property is lowered; and
a function generator electrically connected to the counter electrode and configured to apply an AC potential signal to the counter electrode,
wherein the impedance microscope is configured to:
acquire an output signal associated with the AC potential signal guided to the conductive thin film via the localized region;
measure an impedance value corresponding to the localized region based on the output signal; and
form an image based on the impedance value.

15. The impedance microscope according to claim 14, further comprising a second insulating thin film, the first main surface of the insulating thin film facing the second insulating thin film, wherein
the counter electrode includes a conductive thin film electrode disposed along the second insulating thin film, and
the function generator applies the AC potential signal to the conductive thin film electrode.

16. The impedance microscope according to claim 14, wherein
the counter electrode includes a probe having a needle-shape, and
the function generator applies the AC potential signal to the probe.

17. The impedance microscope according to claim 14, further comprising a power supply to apply a bias voltage to the conductive thin film.

18. The impedance microscope according to claim 17, further comprising
a second power supply to apply a second bias voltage to the counter electrode.

19. The impedance microscope according to claim 18, further comprising a bias adjustment circuit to adjust the bias voltage applied to the conductive film and to adjust the second bias voltage applied to the counter electrode so that an SN ratio of the output signal is equal to or greater than a predetermined value.

* * * * *